(12) United States Patent
Gerardos et al.

(10) Patent No.: US 12,085,562 B2
(45) Date of Patent: Sep. 10, 2024

(54) APPARATUS

(71) Applicant: GREAT NORTH RESEARCH AND INNOVATION LTD, Tyne And Wear (GB)

(72) Inventors: Georgios Gerardos, Tyne And Wear (GB); Dan Haworth, Cambridgeshire (GB); Paul Scott, Cambridgeshire (GB); Will Harris, Suffolk (GB); Leigh Shelford, Cambridgeshire (GB)

(73) Assignee: Great North Research and Innovation Ltd, Tyne And Wear (GB)

( * ) Notice: Subject to any disclaimer, the term of this patent is extended or adjusted under 35 U.S.C. 154(b) by 785 days.

(21) Appl. No.: 17/293,220

(22) PCT Filed: Nov. 11, 2019

(86) PCT No.: PCT/GB2019/053185
§ 371 (c)(1),
(2) Date: May 12, 2021

(87) PCT Pub. No.: WO2020/099844
PCT Pub. Date: May 22, 2020

(65) Prior Publication Data
US 2021/0382047 A1    Dec. 9, 2021

(30) Foreign Application Priority Data

Nov. 13, 2018  (GB) .................................. 1818478

(51) Int. Cl.
*B01L 3/00* (2006.01)
*B01F 23/00* (2022.01)
(Continued)

(52) U.S. Cl.
CPC ....... *G01N 33/54386* (2013.01); *G01N 35/04* (2013.01); *G01N 35/1009* (2013.01);
(Continued)

(58) Field of Classification Search
CPC ............. G01N 33/54386; G01N 35/04; G01N 35/1009; G01N 35/1079;
(Continued)

(56) References Cited

U.S. PATENT DOCUMENTS

2018/0267068 A1*  9/2018  Mori .................... G01N 35/025

FOREIGN PATENT DOCUMENTS

AU    2017210511 A1   8/2017
EP       3270168 A1   1/2018
(Continued)

OTHER PUBLICATIONS

International Search Report and Written Opinion of the International Searching Authority, issued in PCT/GB2019/053185, mailed Mar. 4, 2020; ISA/EP.

*Primary Examiner* — Jennifer Wecker
*Assistant Examiner* — Oyeleye Alexander Alabi
(74) *Attorney, Agent, or Firm* — Harness, Dickey & Pierce, PLC

(57) ABSTRACT

The present invention relates to a biochemical assay apparatus in which a sample processing device is controlled by a detection instrument through a series of linear and rotary actuations to execute a biochemical assay on a biological fluid sample.

21 Claims, 15 Drawing Sheets

(51) Int. Cl.
| | |
|---|---|
| *B01F 23/41* | (2022.01) |
| *B01F 101/23* | (2022.01) |
| *B23Q 17/24* | (2006.01) |
| *C12M 1/34* | (2006.01) |
| *C12Q 1/04* | (2006.01) |
| *C12Q 1/18* | (2006.01) |
| *C12Q 1/686* | (2018.01) |
| *G01N 21/3577* | (2014.01) |
| *G01N 21/359* | (2014.01) |
| *G01N 21/39* | (2006.01) |
| *G01N 21/45* | (2006.01) |
| *G01N 21/64* | (2006.01) |
| *G01N 30/12* | (2006.01) |
| *G01N 30/68* | (2006.01) |
| *G01N 30/70* | (2006.01) |
| *G01N 30/72* | (2006.01) |
| *G01N 30/88* | (2006.01) |
| *G01N 33/00* | (2006.01) |
| *G01N 33/18* | (2006.01) |
| *G01N 33/50* | (2006.01) |
| *G01N 33/543* | (2006.01) |
| *G01N 33/68* | (2006.01) |
| *G01N 35/04* | (2006.01) |
| *G01N 35/10* | (2006.01) |

(52) U.S. Cl.
CPC . *G01N 35/1079* (2013.01); *G01N 2035/0441* (2013.01); *G01N 2035/1032* (2013.01); *G01N 2035/1062* (2013.01)

(58) Field of Classification Search
CPC ... G01N 2035/0441; G01N 2035/1032; G01N 2035/1062; G01N 33/53; G01N 33/5302; G01N 33/543; G01N 2035/1044
See application file for complete search history.

(56) References Cited

FOREIGN PATENT DOCUMENTS

| | | |
|---|---|---|
| EP | 3301454 A1 | 4/2018 |
| GB | 2521885 A | 7/2015 |
| KR | 20140017418 A | 2/2014 |

* cited by examiner

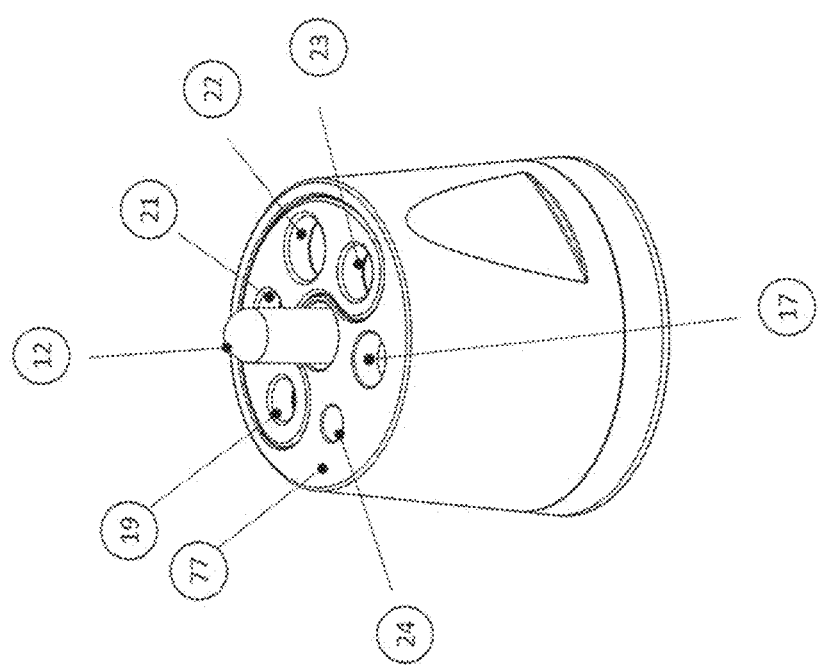
Figure 2.c

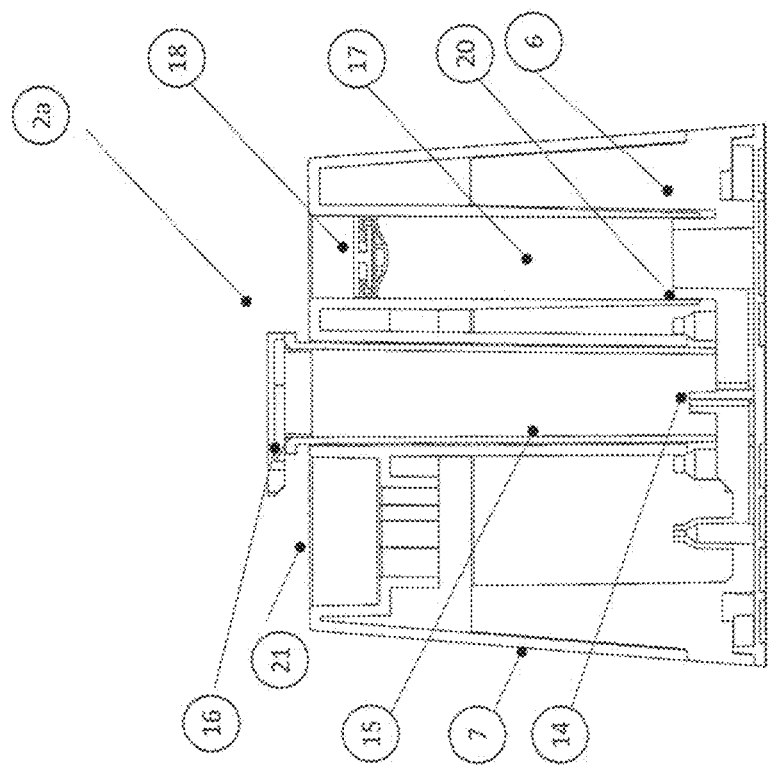
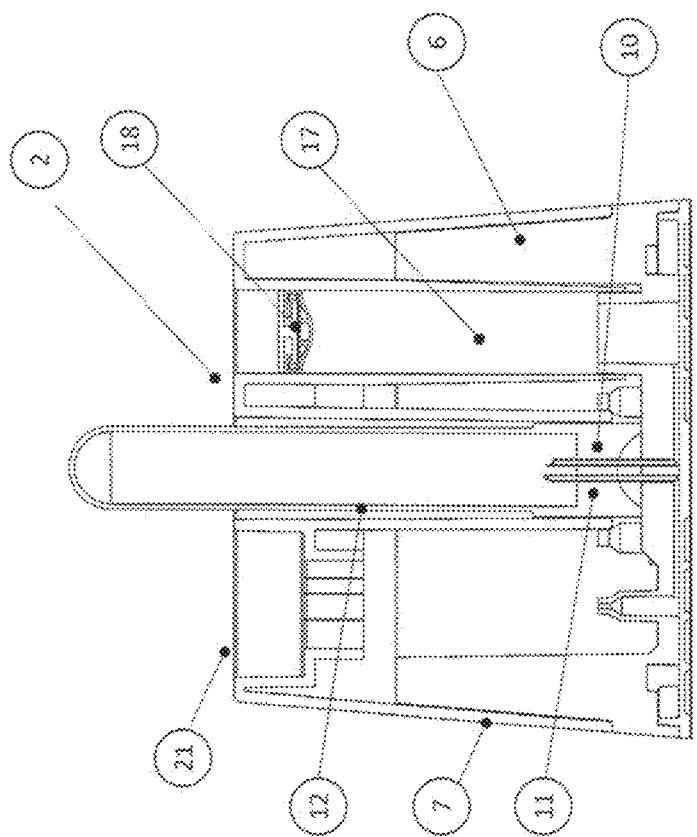

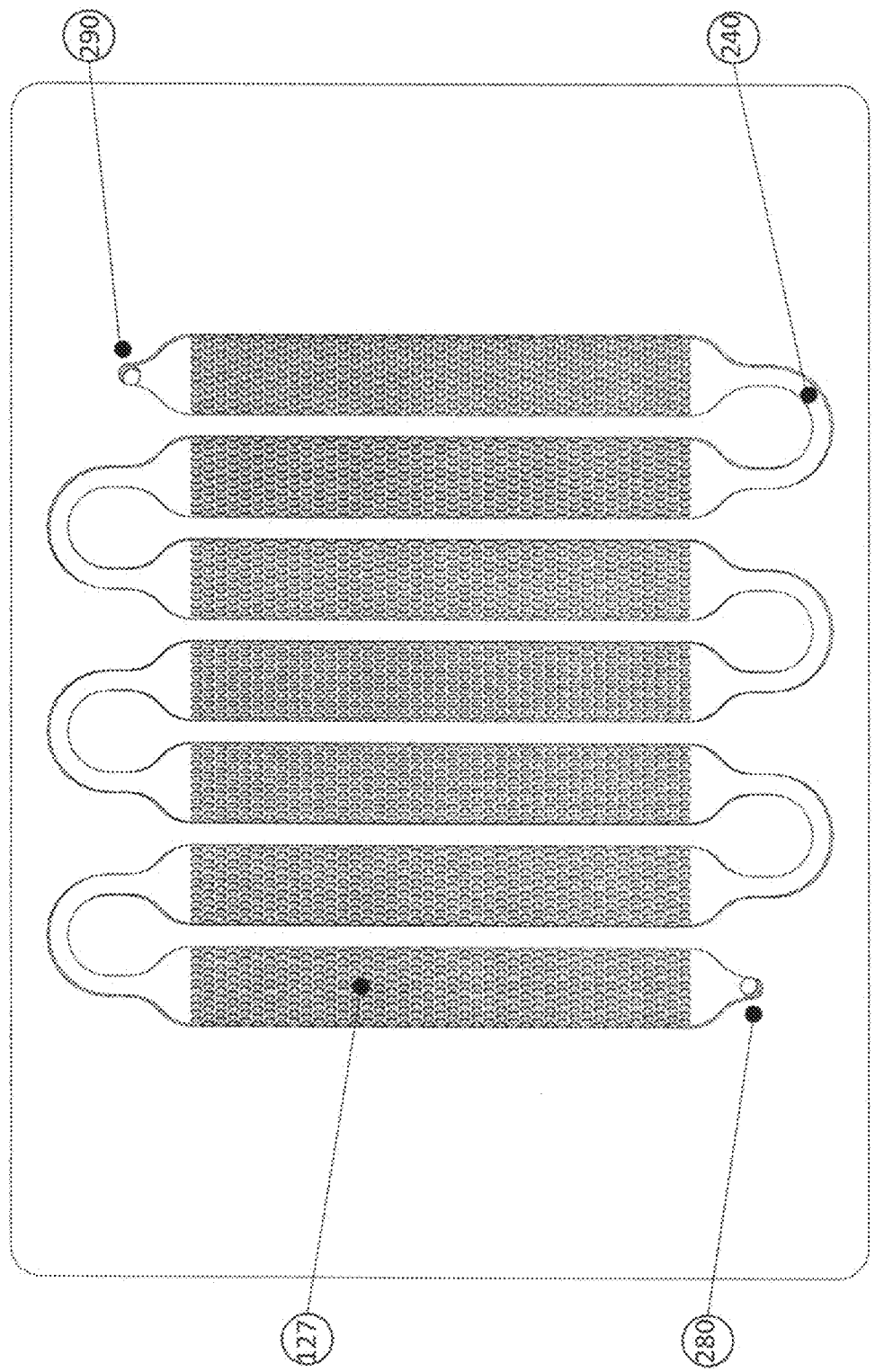

APPARATUS

CROSS-REFERENCE TO RELATED APPLICATIONS

This application is a 371 U.S. National Phase of International Application No. PCT/GB2019/053185, filed Nov. 11, 2019, which claims priority to British Patent Application No. GB 1818478.8, filed Nov. 13, 2018. The entire disclosures of the above applications are incorporated herein by reference.

The present invention relates to a biochemical assay apparatus.

A biochemical assay is an analytical procedure used in inter alia laboratory medicine, pharmacology, environmental biology or molecular biology for qualitatively or quantitatively measuring the presence, amount or functional activity of a biochemical analyte in a sample.

Although biochemical assays are numerous and diverse, the steps of the analysis are generally (a) sample processing and manipulation to selectively present the analyte in a measurable form to a detection system, (b) identifying the analyte in the sample by a specific attribute, (c) converting the presence or quantity of the analyte into a detectable signal and (d) detecting the detectable signal and associating the detectable signal with an interpretable attribute that can be quantitative or qualitative.

To achieve these steps, an assay device comprises generally a means for sample processing and a means for detection (eg a reader). An example of an immunoassay device is disclosed in GB-A-2521885.

The present invention seeks to improve the performance of a biochemical assay by integrating sample processing with a detection instrument. More particularly, the present invention relates to an apparatus in which a sample processing device is controlled by the detection instrument through a series of linear and/or rotary actuations to execute a biochemical assay on a biological fluid sample.

Thus viewed from one aspect the present invention provides a biochemical assay apparatus for assaying a biological fluid sample comprising:
a detection instrument which comprises:
  an enclosure;
  a movable platform in the enclosure selectively movable to a plurality of positions;
  a linear actuator mounted in the enclosure above the movable platform and actuatable along a linear axis;
a sample processing device mounted or mountable on the movable platform in the enclosure which comprises:
  a manifold;
  a compartmentalised housing mounted on the manifold and capable of receiving the biological fluid sample in an elongate fluid compartment, wherein the compartmentalised housing has a valve compartment, a rack compartment and an elongate air chamber which is sealed by an air plunger;
  a rack of elongate vessels mounted in the rack compartment at an elevated non-deployed position or at a non-elevated deployed position, wherein each elongate vessel defines a fluid chamber which is sealed by a fluid plunger, wherein the rack of elongate vessels is movable from the elevated non-deployed position to the non-elevated deployed position to cause the elongate vessels to fluidly connect to the manifold;
  an antibody array mounted beneath a floor of the manifold such that the manifold is able to fluidly couple each elongate vessel selectively to the antibody array; and
  an array valve which has a closed position which isolates the elongate vessels from the antibody array and an open position which fluidly connects the elongate vessels to the antibody array via the manifold,
wherein when the rack of elongate vessels is in the non-elevated deployed position, the movable platform is moved sequentially to selected ones of the plurality of positions,
wherein in an initial position of the plurality of positions, the linear actuator is substantially coaxial with the elongate air chamber whereby on actuation the linear actuator depresses the air plunger to cause air from the elongate air chamber to enter the elongate fluid compartment and flush the biological fluid sample into a first fluid chamber of a first elongate vessel of the rack of elongate vessels containing a first diluent reagent to form a diluted biological fluid sample,
wherein in a first position of the plurality of positions, the linear actuator is substantially coaxial with the first fluid chamber of the first elongate vessel whereby on actuation the linear actuator depresses the fluid plunger of the first elongate vessel to cause the diluted biological fluid sample to enter the antibody array via the manifold,
wherein in a second position of the plurality of positions, the linear actuator is substantially coaxial with a second fluid chamber of a second elongate vessel of the rack of elongate vessels whereby on actuation the linear actuator depresses the fluid plunger of a second elongate vessel to cause a wash reagent to enter the antibody array via the manifold and
wherein in a third position of the plurality of positions, the linear actuator is substantially coaxial with a third fluid chamber of a third elongate vessel of the rack of elongate vessels whereby on actuation the linear actuator depresses the fluid plunger of the third elongate vessel to cause an assay label reagent to enter the antibody array via the manifold.

In a preferred embodiment, the movable platform is a rotary platform selectively rotational to a plurality of rotary positions. The linear axis of the linear actuator may be substantially parallel to and spaced apart from the rotary axis of the rotary platform.

In a preferred embodiment, the movable platform is an x-y platform (or x-y stage) selectively movable to a plurality of x-y positions. The linear axis of the linear actuator may be substantially parallel to the z axis of the x-y platform.

Preferably in a fourth position of the plurality of positions, the linear actuator is substantially coaxial with a fourth fluid chamber of a fourth elongate vessel of the rack of elongate vessels whereby on actuation the linear actuator depresses the fluid plunger of the fourth elongate vessel to cause an additional wash reagent to enter the antibody array via the manifold.

The biochemical assay apparatus of the invention advantageously facilitates point-of-care diagnosis.

The array valve may be a fluid pressure valve which opens at a threshold fluid pressure or an umbrella valve. The umbrella valve may be at or near to an array inlet port of the antibody array.

Preferably the array valve is an actuatable array valve mounted in the valve compartment. Typically the actuatable array valve includes a valve plunger.

In a particularly preferred embodiment when the rack of elongate vessels is in the non-elevated deployed position, the movable platform is additionally movable to a valve position of the plurality of positions, wherein in the valve position the linear actuator is substantially coaxial with the valve compartment whereby on actuation the linear actuator actuates the actuatable array valve to the open position to fluidly connect the elongate vessels and the antibody array via the manifold.

The actuatable array valve may comprise a valve stem, a valve cap and a valve plunger. The valve stem may be part of the manifold and contain a substantially central bore with a groove that stops substantially mid-way along the central bore. An outlet channel may be substantially parallel to the central bore. The valve plunger may provide a liquid-tight seal in the central bore above the groove. The valve plunger may have an interference-type fit such that it can be pushed downwardly by the valve cap to the location of the groove.

The valve cap may include a wiper seal that seals the valve stem circumferentially and a pusher that actuates the valve plunger. When the array valve is closed, the valve cap and the valve plunger may be in an elevated position where the central bore is blocked. The actuatable array valve is opened when the linear actuator actuates the valve cap which displaces the valve plunger in the central bore. This allows fluid communication to the outlet channel. The outlet channel fluidly couples the manifold to the antibody array.

Preferably the antibody array is mounted sealingly beneath the floor of the manifold. The antibody array may be fluidly sealed to the manifold by mechanical means (such as a Luer-type connector or spigot) or by bonding (such as laser bonding or adhesive bonding).

Preferably the antibody array includes one or more channels which create a continuous fluid pathway between an array inlet port and an array outlet port, wherein antibodies are attached to the walls and/or floor of the channel. An array cover may be mounted on the base of the antibody array (eg by a fastener or by bonding such as laser bonding or adhesive bonding) to seal the channel and prevent leakage.

In a preferred embodiment, prominences (eg ribs or pillars) are provided on the walls or floor of the channel. This serves to increase the surface area exposed to the biological fluid sample. Particularly preferably the prominences are mutually spaced apart (eg randomly or non-randomly). By spacing the prominences apart, the flow of fluid may be disrupted to promote the interaction between an analyte (eg a target pathogen) in the biological fluid sample and antibodies on the walls or floor of the fluid channel.

The fluid channel may have a uniform cross-section. The fluid channel may have a rectangular or oval cross-section.

The fluid pathway may be tortuous. Preferably the fluid pathway is a spiral or zig-zag fluid pathway.

Preferably fluid is discharged from the array outlet port into a waste chamber in the manifold (eg in the peripheral region of the manifold). A hydrophobic frit or vent can be included in the top of the waste chamber to relieve air pressure.

The antibody array may comprise a control zone on to which a probe capture ligand is immobilised and a first major surface on which two or more test zones are defined, wherein a first test zone has immobilised thereon a first pathogen-specific antibody adapted to bind to a first capture target on a first pathogen or marker, wherein a second test zone has immobilised thereon a second pathogen-specific antibody adapted to bind to a second capture target on a second pathogen or marker.

The housing may have a partial lid. For example, the lid may have an arcuate aperture. The rack of elongate vessels may be inserted through the arcuate aperture. The elongate air chamber and valve compartment may be accessible through apertures in the lid.

The housing may be slidably mounted on the manifold (eg the exterior of the manifold).

Preferably the manifold contains a fluid circuit which is able to fluidly couple each of the elongate vessels to the antibody array.

Preferably the rack of elongate vessels comprises a plurality of substantially cylindrical vessels mutually spaced apart and connected at their neck portions by a collar. Typically the rack of elongate vessels has four elongate vessels defining respectively the first chamber, second chamber, third chamber and fourth chamber. The collar may be an arcuate or box-like collar.

In the elevated non-deployed position, the rack of elongate vessels is seated in the rack compartment and each elongate vessel is aligned with and spaced apart from a spigot or needle projecting upwardly from the floor of the manifold. The rack of elongate vessels may be depressed to a non-elevated deployed position such that the foot end of the elongate vessel is penetrated by the spigot or needle.

In the non-elevated deployed position, the rack of elongate vessels is restrained vertically by the housing. The rack of elongate vessels may be restrained vertically by a clip mounted on the exterior surface of the rack of elongate vessels. Alternatively the rack of elongate vessels may be restrained vertically by latching with the manifold.

Each elongate vessel may be equipped at its foot end with a stopper, a syringe end cap or a frangible member (eg a foil or film).

Preferably each elongate vessel is equipped at its foot end with a stopper. As the rack of elongate vessels moves to the non-elevated deployed position, the spigot dislodges the stopper to open a fluid pathway between the elongate vessel and the manifold (eg the fluid circuit). The stopper may be dislodged into the lower portion of the elongate vessel. A feature (eg a groove or castellation) may be provided on an upper surface of the spigot to prevent the stopper from blocking the fluid pathway between the elongate vessel and the manifold (eg fluid circuit).

The sample of a biological fluid may be provided in the fluid compartment in a vacutainer. The vacutainer may be inserted into the sample processing device through a vacutainer port in the housing (eg in the lid).

Alternatively a sample vessel containing a cap may be sealed to the manifold to form the fluid compartment. The sample vessel may be charged with the biological fluid sample by a user.

In a preferred embodiment, the manifold contains a first and second hollow needle projecting upwardly from its floor. The first and second needles may be substantially coincident with the main axis (eg the z axis or axis of rotation) of the sample processing device. The first and second needles may be adapted to puncture the vacutainer (eg a septum of the vacutainer). The first needle may be in fluid communication with the first chamber. The second needle may be in fluid communication with the air chamber. The second needle may be at a different height to the first needle to prevent air from the air chamber bypassing directly into the first needle.

In an alternative preferred embodiment, a first fluid aperture and a second fluid aperture are included in the manifold (eg in the fluid circuit). The first and second fluid apertures may be at different heights to prevent air from the air chamber passing directly therebetween.

When the linear actuator depresses the air plunger, air from the air chamber may enter the fluid compartment via the second needle and flush the biological fluid sample into the first chamber via the first needle and a bore in the spigot. The air plunger may be non-retractable. For example, the air plunger may interface with a detent which locks the air plunger at the bottom-stroke. Alternatively a one-way valve such as a duck-bill, dome valve or similar may be included in the air chamber to prevent fluid backflow into the air chamber.

The fluid plunger in the first chamber may be located initially in a substantially mid-stroke location. The first chamber may include a height stop that stops the fluid plunger at the top-stroke. This prevents the fluid plunger from exiting the first chamber.

The fluid plunger in each of the second, third and fourth chambers may be located initially in a substantially top-stroke location. Each of the second, third and fourth chambers may include an internal detent that stops the fluid plunger at the top-stroke. This prevents the biological fluid sample from entering the second, third and fourth chambers.

Each of the first, second, third and fourth chambers may include an internal detent that locks the fluid plunger at the bottom-stroke. This prevents the plunger from being retracted.

The detection instrument may be equipped with an electrical power cable and connectivity ports (eg USB ports) to connect to peripherals. The peripherals may include a barcode scanner, printer and local area network. The detection instrument may include optical or proximity sensors to confirm the presence of the sample processing device and an exterior touch screen which serves as a user interface.

The detection instrument may comprise a door to close the enclosure.

The detection instrument may include an actuator that drives the movable platform.

In a preferred embodiment, the air chamber, the valve compartment and the first, second, third and fourth chambers define a pitch circle with a substantially common diameter. When the sample processing device is mounted on a rotary platform, the pitch circle is intersected by the linear axis of the linear actuator so that as the sample processing device rotates, the air plunger, the valve plunger and the fluid plunger of each of the first, second, third and fourth chambers is substantially aligned beneath the linear actuator.

In a preferred embodiment, the air chamber, the valve compartment and the first, second, third and fourth chambers define a rectangular array. When the sample processing device is mounted on a x-y platform, the rectangular array is intersected by the linear axis of the linear actuator so that as the sample processing device moves, the air plunger, the valve plunger and the fluid plunger of each of the first, second, third and fourth chambers is substantially aligned beneath the linear actuator.

The linear actuator and movable platform may include position sensors which coordinate the actuation of the fluid plungers, the air plunger or the valve plunger in each of the plurality of positions.

Typically an optical module is located in the basal part of the detection instrument. The optical module may be a fluorescent or IR imager or a laser which images the bottom surface of the antibody array. The optical module may be adapted to image magnetic labels.

The analyte may be a cellular analyte (such as a microbe, bacteria, fungi or virus), a unicellular protozoa, Eukaryotic cells of human or non-human origin (eg human cancer cells) or organic or inorganic molecules.

The antibodies may be adapted to selectively bind to a target molecule in the analyte. The antibodies may be immunoglobulins, affimers or aptamers.

Viewed from a further aspect the present invention provides a sample processing device as hereinbefore defined.

Viewed from a yet further aspect the present invention provides a detection instrument as hereinbefore defined.

The present invention will now be described in a non-limitative sense with reference to the accompanying Figures in which:

FIGS. 2a and 2c illustrate the sample processing device of the embodiment shown in FIG. 1 in a disassembled and assembled state respectively;

FIGS. 2b-1 and 2b-2 illustrate a cross-sectional view of the sample processing device shown in FIG. 2c before and after deployment of the vessel rack respectively and before being loaded with a vacutainer;

FIG. 3a illustrates a cross-sectional view of the sample processing device shown in FIG. 2c after being loaded with a vacutainer;

FIG. 3b illustrates a cross-sectional view of an alternative embodiment of the sample processing device;

Figure 7C:
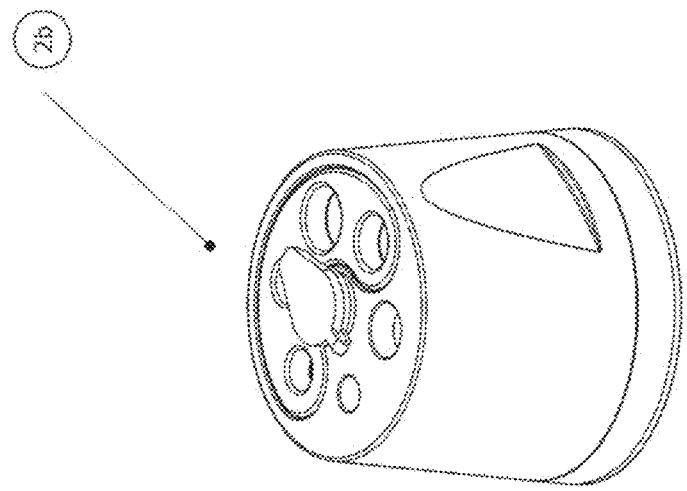
Figure 7B:
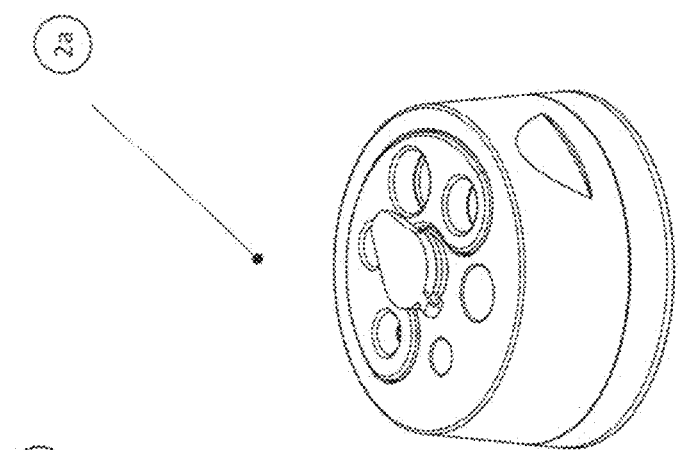
Figure 7A:
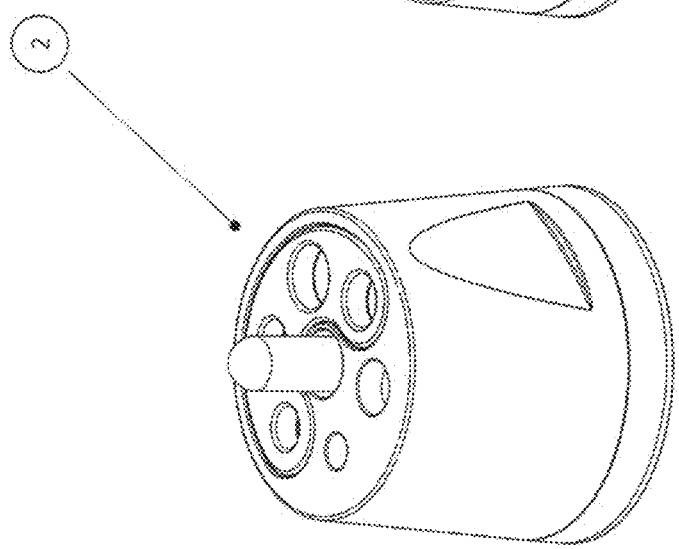
Figure 8:
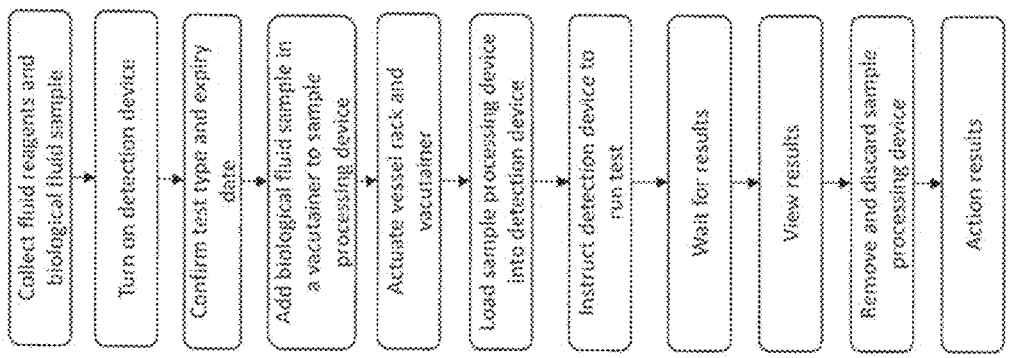
Figure 9:
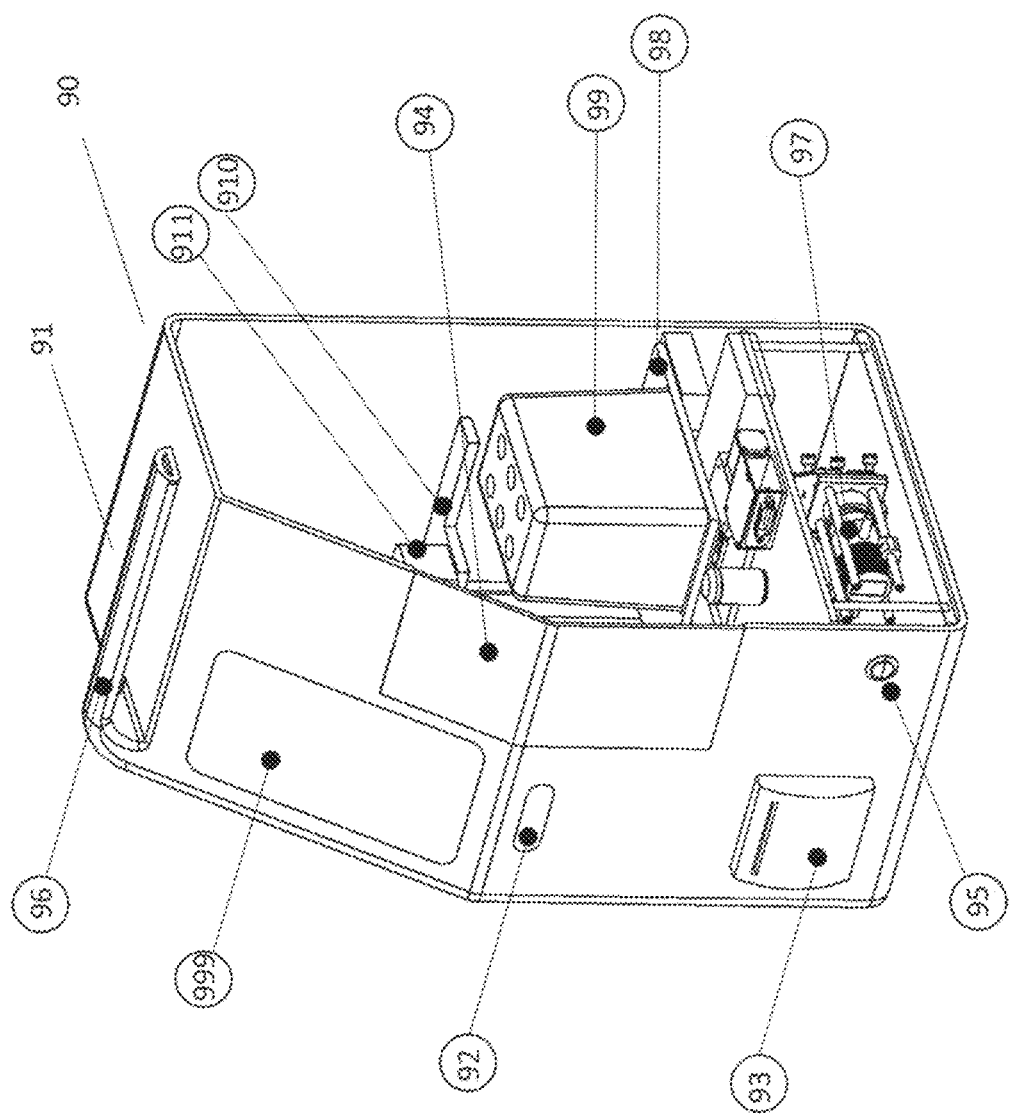
Figure 10:
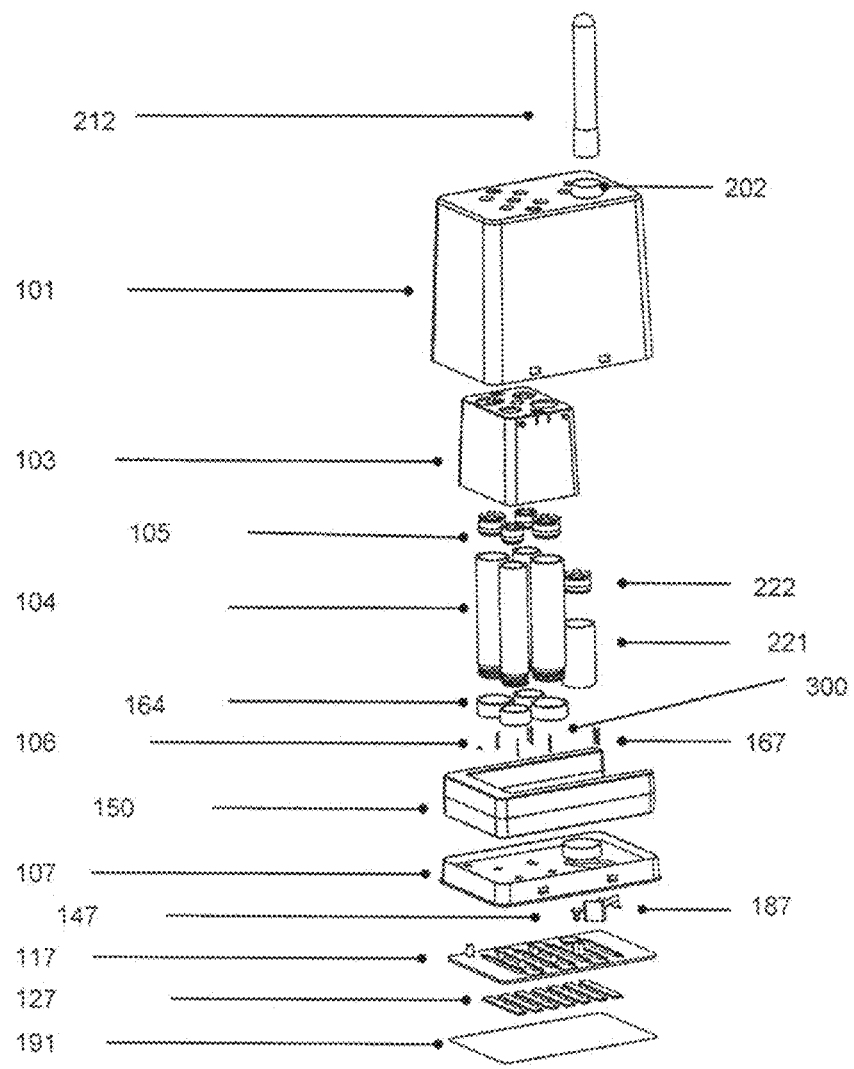

FIGS. 7a-c illustrate various embodiments of the sample processing device;

FIG. 8 illustrates schematically a test carried out using the biochemical assay apparatus of the invention;

FIG. 9 illustrates in cross-section an alternative embodiment of the biochemical assay apparatus of the invention;

FIG. 10 illustrates the sample processing device of the embodiment shown in FIG. 9 in a disassembled state; and FIG. 11 illustrates the antibody array of the sample processing device shown in FIG. 10.

Figure 1:
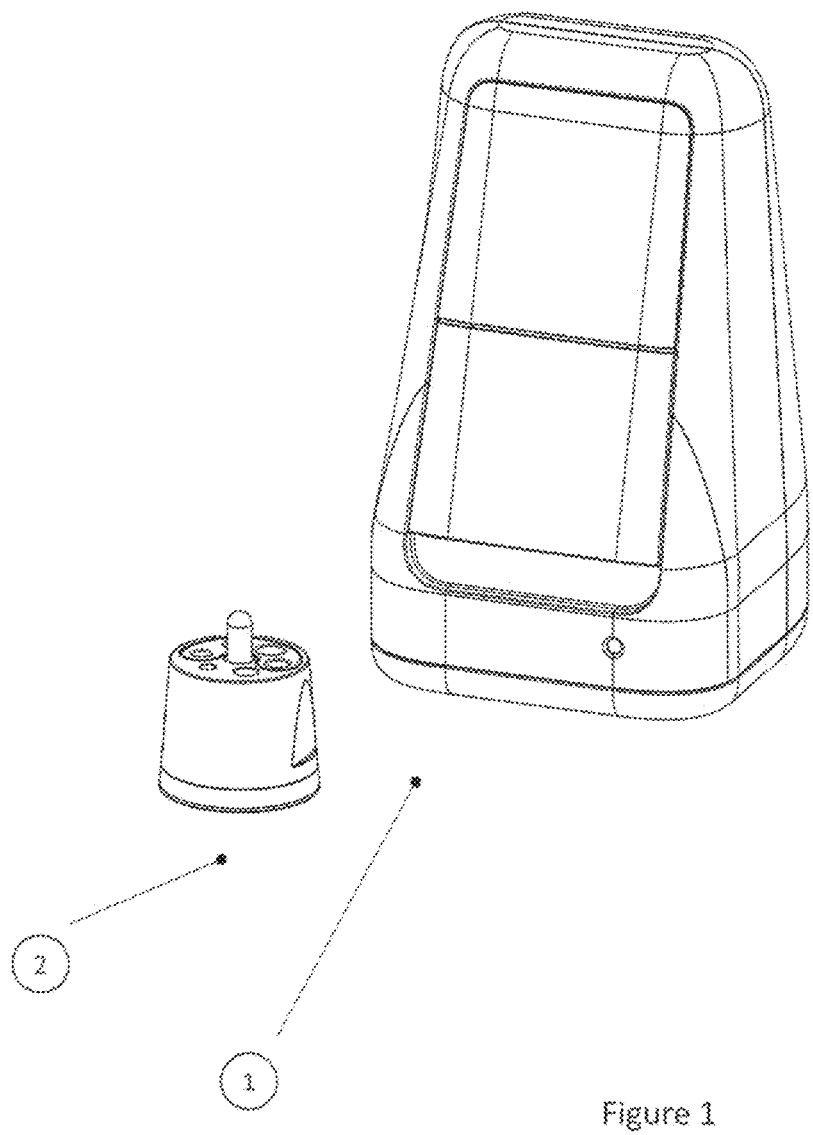
FIG. 1 illustrates an embodiment of the biochemical assay apparatus of the invention.

FIG. 1 illustrates an embodiment of the biochemical assay apparatus of the invention which comprises generally a detection instrument (1) and a sample processing device (2) which is controlled by the detection instrument (1) through a series of linear and rotary actuations to execute a biochemical assay on a biological fluid sample.

Figure 2A:
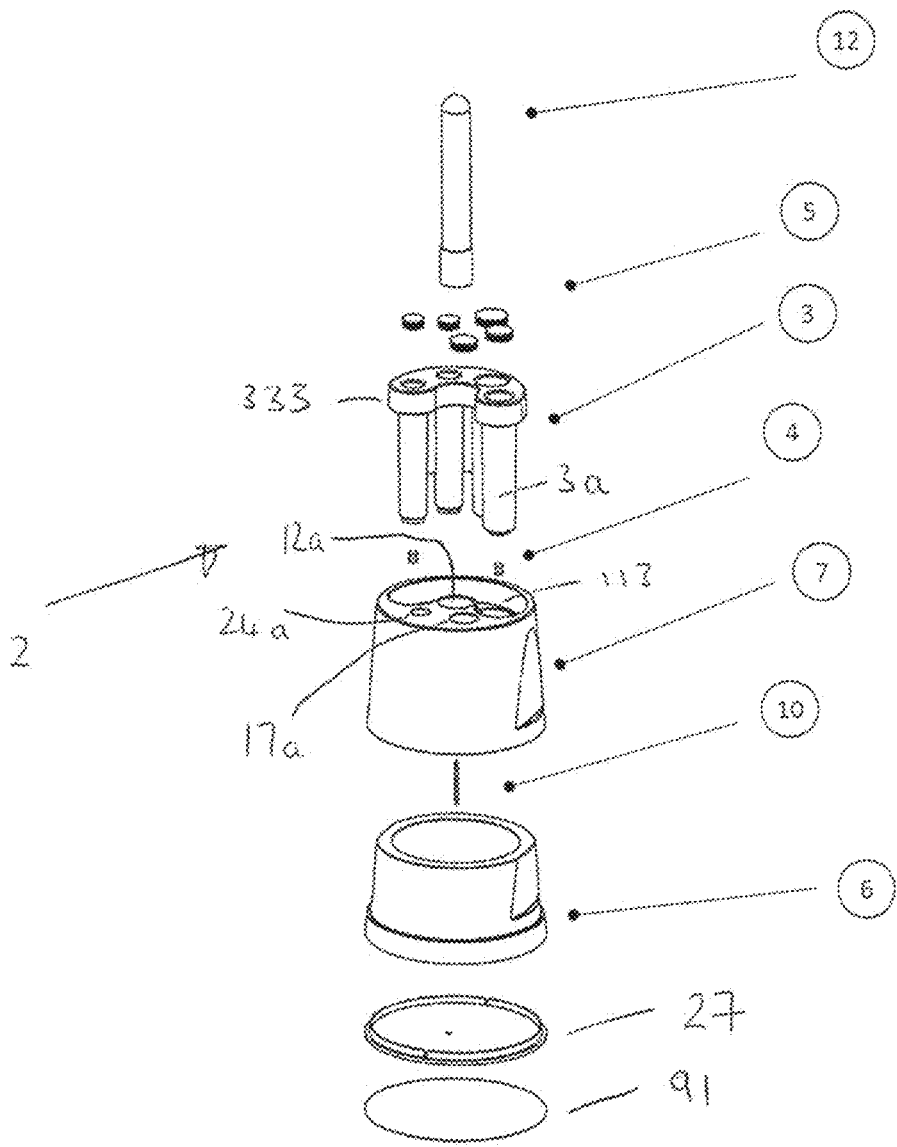

The sample processing device (2) is a single-use consumable which contains the fluid reagents (eg functionalised elements, buffers and labels) necessary to execute the biochemical assay on the biological fluid sample. With reference to FIG. 2a, the sample processing device (2) comprises a housing (7) and a vessel rack (3) vertically restrainable in a rack compartment of the housing (7).

The vessel rack (3) comprises four substantially cylindrical vessels (3a) mutually spaced apart and connected at their neck portions by an arcuate collar (333). Each vessel (3a) is equipped at its foot end with a stopper (4) and at its head end with a fluid plunger (5). As shown in FIG. 2c, the four vessels (3a) define respectively a first chamber (19) for a dilution buffer, a second chamber (21) for a first wash buffer, a third chamber (22) for an assay label and a fourth chamber (23) for a second wash buffer. The vessel rack (3) is inserted through a complementarily-shaped arcuate aperture (113) in a lid (77) of the housing (7).

The housing (7) is mounted slidably on the exterior of a manifold (6). The manifold (6) contains a fluid circuit (32) which is able to fluidly couple the first, second, third and fourth chambers (19, 21, 22 and 23) to an antibody array (27) mounted sealingly beneath the floor of the manifold (6). The fluid circuit (32) is sealed from the chambers (19, 21, 22 and 23) of the vessels (3a) until the point of use when it is selectively fluidly connected to each vessel (3a) as described hereinafter. The housing (7) additionally defines an air chamber (17) and a valve compartment (24) for an array valve (26). The air chamber (17) and valve compartment (24) are accessible respectively through apertures (17a, 24a) in the lid (77) of the housing (7). The air chamber (17) is sealed by an air plunger (18).

Figure 4B:
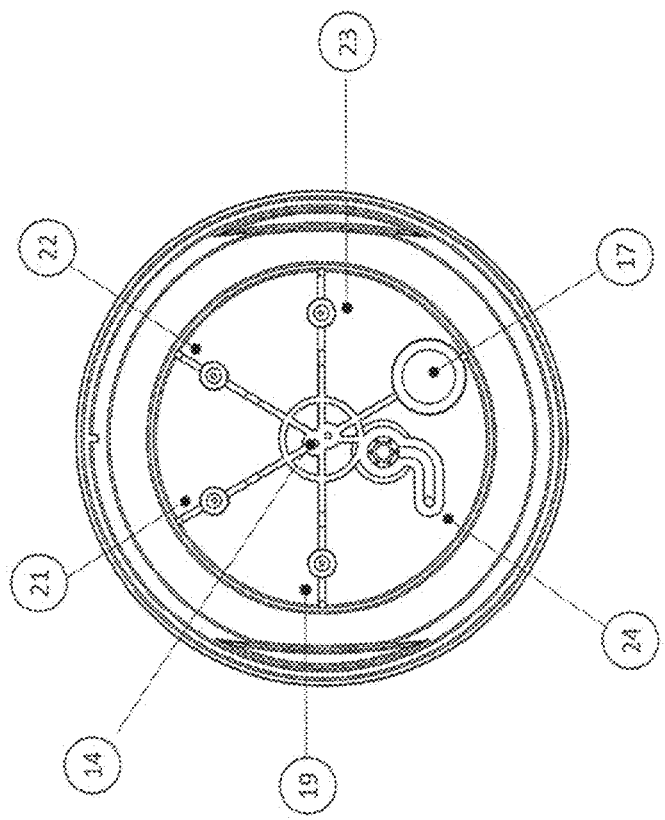
FIGS. 4a and 4b illustrate beneath the floor of the manifold of the sample processing device of FIGS. 3a and 3b respectively.
Figure 4A:
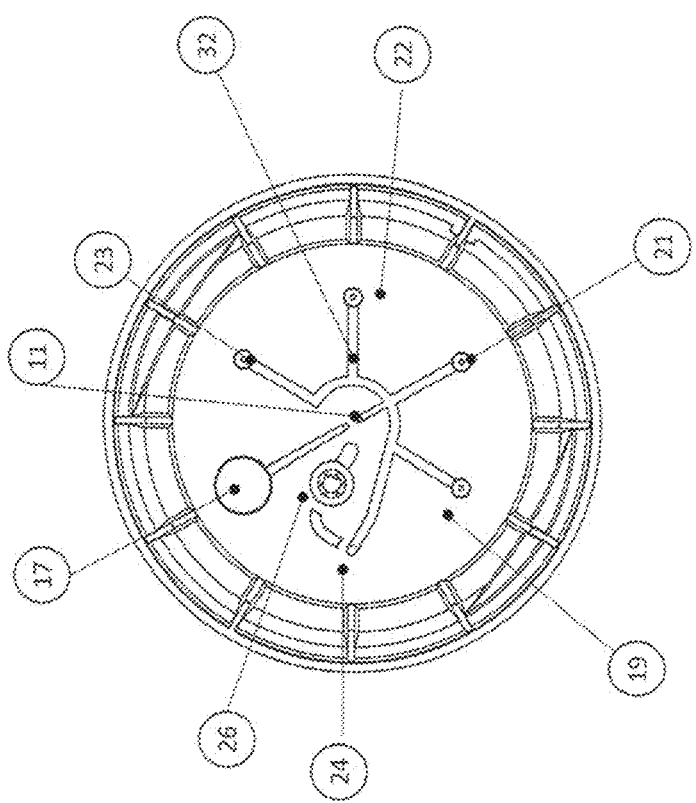
Figure 4C:
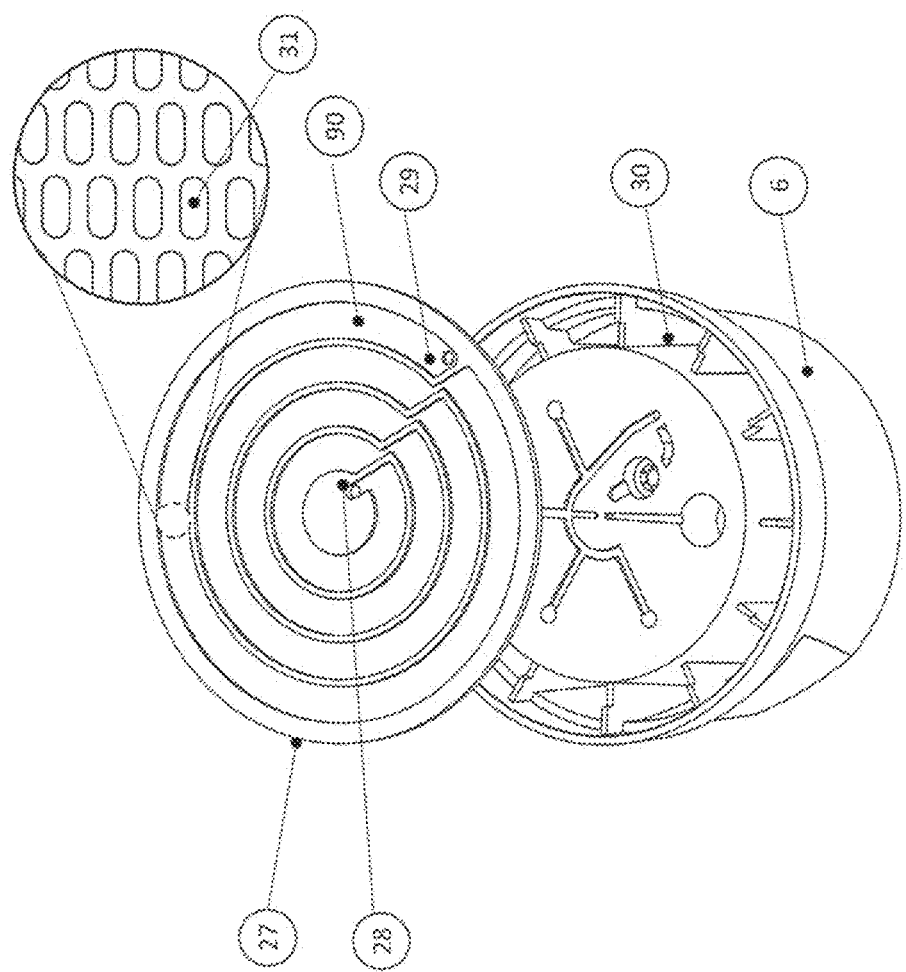
FIG. 4c illustrates the antibody array of the sample processing device shown in FIG. 2c dismounted from beneath the floor of the manifold.

An array inlet port (28) in the antibody array (27) is normally isolated from the fluid circuit (32) by the array valve (26) which is located upstream from the array inlet port (28) (see FIGS. 4a and 4c). The antibody array (27) comprises a spiral channel (90) which creates a continuous fluid pathway between the array inlet port (28) and an array outlet port (29) from where fluid is discharged into a waste chamber (30) in the peripheral region of the manifold (6). Antibodies are attached to the walls of the channel (90). Ribs (31) on the floor of the channel (90) serve to increase the surface area exposed to the fluid and to disrupt the flow of the fluid so as to promote the interaction of analytes (eg pathogens) with the antibodies attached to the walls. The antibody array (27) is fluidly sealed to the manifold (6) by mechanical means such as Luer-type connectors or spigots or by laser bonding or an adhesive. An array cover (91) is mounted on the base of the antibody array (27) by laser bonding or an adhesive to seal the channel (90) and prevent leakage. The path length and cross-sectional area of the channel (90) are minimised to reduce dead volumes.

Figures 2, 2B:
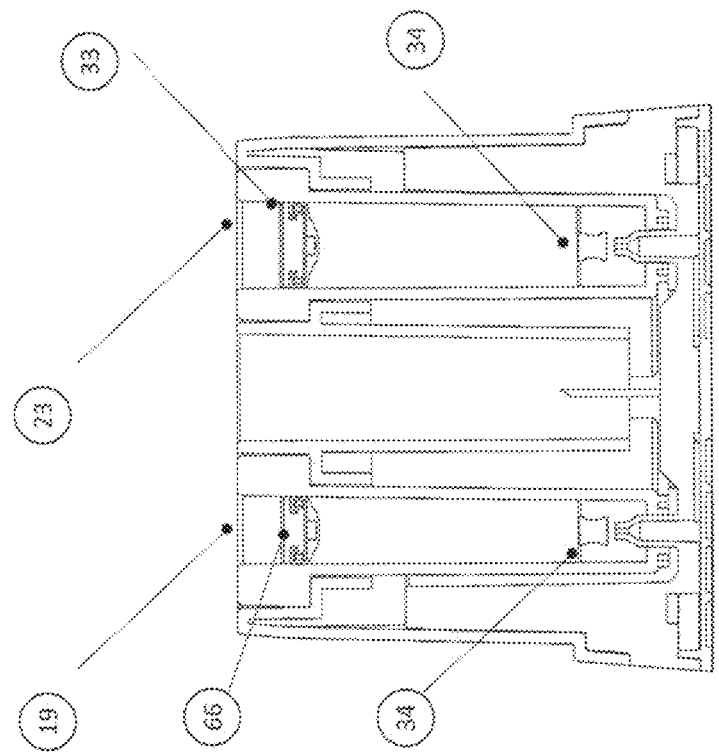
Figures 1, 2B:
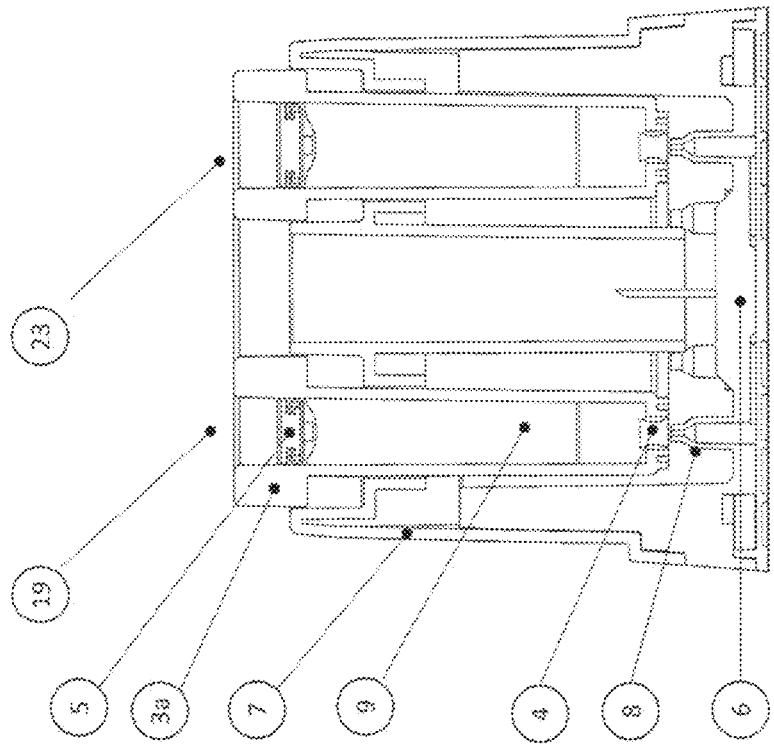

FIG. 2b-1 illustrates a cross-sectional view of the sample processing device (2) with the vessel rack (3) inserted through the complementarily-shaped aperture (113) in the lid (77) in an elevated (non-deployed) position before deployment. In this elevated (non-deployed) position, the vessel rack (3) is seated in the rack compartment of the housing (7) and each vessel (3a) is aligned with and spaced apart from a spigot (8) projecting upwardly from the floor of the manifold (6). At the point-of-use, the vessel rack (3) is depressed to a non-elevated (deployed) position such that the foot end of the vessel (3a) is penetrated by the spigot (8) (see FIG. 2b-2). In the non-elevated (deployed) position, the vessel rack (3) is restrained by the housing (7). The spigot (8) displaces the stopper (4) to open a fluid pathway between the vessel (3a) and the fluid circuit (32). The stopper (4) is dislodged into the lower portion of the vessel (3a). A groove on the top surface of the spigot (8) serves to prevent the stopper (4) from blocking the fluid pathway between the vessel (3a) and the fluid circuit (32).

FIG. 3a illustrates a cross-sectional view of the sample processing device (2) shown in FIG. 2c in a sealed state after being loaded with a standard vacutainer (12). The vacutainer (12) containing a biological fluid sample is inserted into the sample processing device (2) through a vacutainer port (12a) in the lid (77). The manifold (6) contains a first and second hollow needle (10, 11) projecting upwardly from its floor and substantially coincident with the main axis of rotation of the sample processing device (2). The first and second needles (10, 11) are adapted to puncture the septum of the vacutainer (12). The first needle (10) is in fluid communication with the first chamber (19). The second needle (11) is in fluid communication with the air chamber (17). The second needle (11) is at a different height to the first needle (10) to prevent air from the air chamber (17) bypassing directly into the first needle (10).

FIG. 3b illustrates a cross-sectional view of an alternative embodiment of the sample processing device (2a). In this embodiment, a pair of fluid apertures (14) are included in the fluid circuit (32) instead of needles. The fluid apertures (14) are at different heights to prevent air from the air chamber (17) passing directly therebetween. A sample vessel (15) containing a cap (16) is sealed to the manifold (6) and can be charged with a biological fluid sample by a user.

When the air plunger (18) is actuated (as described hereinafter), air from the air chamber (17) is forced into the vacutainer (12) via the second needle (11) (or into the sample vessel (15) via one of the fluid apertures (14) in the alternative embodiment) and flushes the biological fluid sample into the first chamber (19) containing dilution buffer via the first needle (10) and a narrow bore in the spigot (8). The air plunger (18) interfaces with a detent (20) which locks the air plunger (18) at the bottom of its stroke so it cannot be retracted by fluid pressure.

In the first chamber (19), the fluid plunger (5) is initially located mid-stroke and travels to expand the volume to contain the dilution buffer and the biological fluid sample. The action of the biological fluid sample entering the first chamber (19) through the narrow bore in the spigot (8) and the expanding volume in the first chamber (19) causes effective mixing of the biological fluid sample and dilution buffer. A height stop (66) prevents the fluid plunger (5) from exiting the first chamber (19). The biological fluid sample is unable to enter the second, third and fourth chambers (21, 22 and 23) due to an internal detent (33) stopping the respective fluid plungers (5) from travelling beyond full stroke.

Figure 5B:
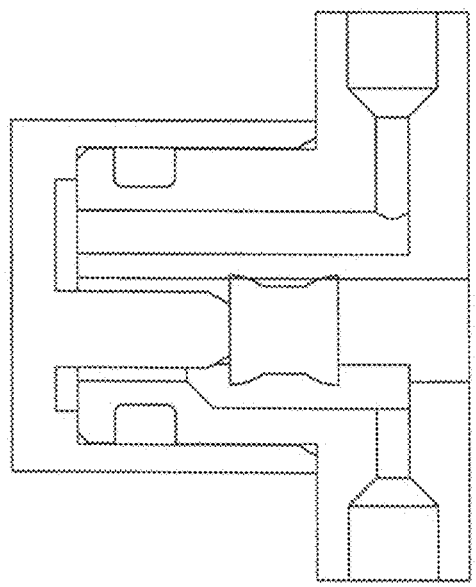
FIGS. 5a and 5b illustrate a cross-sectional view of the valve of the sample processing device shown in FIG. 2c in the closed (non-activated) and open (activated) position respectively.
Figure 5A:
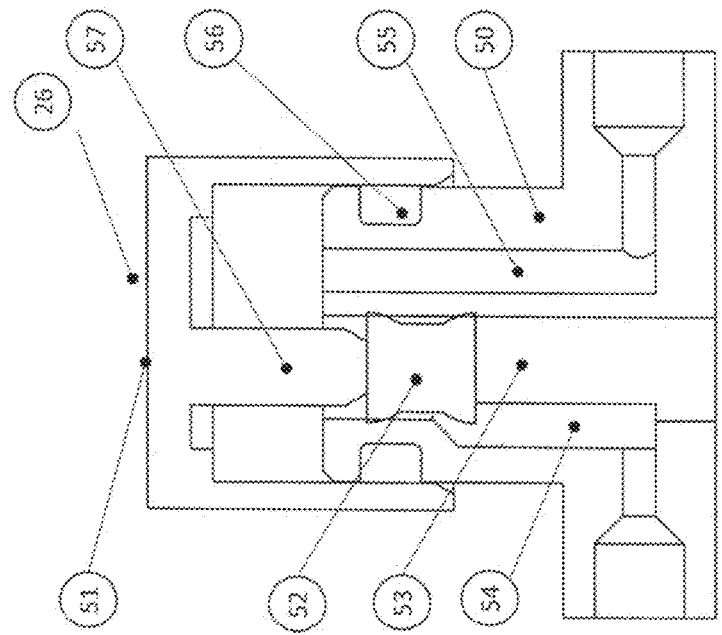

The valve compartment (24) in the housing (7) contains the array valve (26) illustrated in FIGS. 5a and 5b in the closed and open state respectively. The array valve (26) comprises a valve stem (50), a valve cap (51) and a valve plunger (52). The valve stem (50) is part of the manifold (6) and contains a central bore (53) with a groove (54) that stops mid-way along the central bore (53). An outlet channel (55) is parallel to the central bore (53). The valve plunger (52) provides a liquid tight seal in the central bore (53) above the groove (54) and has an interference-type fit such that it can be pushed downwardly by the valve cap (51) to the location of the groove (54). The valve cap (51) includes a wiper seal (56) that seals the valve stem (50) circumferentially and a pusher (57) that actuates the valve plunger (52). When the array valve (26) is closed (see FIG. 5a), the valve cap (51) and the valve plunger (52) are in the elevated position where the central bore (53) is blocked and fluid cannot pass into the outlet channel (55). The array valve (26) is opened by actuating the valve cap (51) (as described hereinafter) which displaces the valve plunger (52) in the central bore (53) and allows fluid communication to the outlet channel (55). The outlet channel (55) fluidly couples the fluid circuit (32) to the array inlet port (28).

With the array valve (26) open, the fluid circuit (32) in the manifold (6) is able to couple selectively the chambers (19, 21, 22 and 23) to the antibody array (27) (see FIGS. 4a to 4c). Firstly the fluid plunger (5) in the first chamber (19) is actuated at a controlled rate (as described hereinafter) and the diluted sample is evacuated into the fluid circuit (32). The diluted sample is then delivered via the array valve (26) through the array inlet port (28) into the antibody array (27). Fluid exits the antibody array (27) through an array outlet port (29) and is discharged into the waste chamber (30). Once the fluid plunger (5) in the first chamber (19) has reached the bottom of its stroke, an internal detent (34) locks the fluid plunger (5) in place so it cannot be retracted by fluid pressure.

The fluid plunger (5) in the second chamber (21) is then actuated at a controlled rate (as described hereinafter) to drive the first wash buffer over the antibody array (27) and into the waste chamber (30). The fluid plunger (5) in the second chamber (21) is locked at the bottom of its stroke by an internal detent (34). The fluid plunger (5) in the third chamber (22) is then actuated at a controlled rate (as described hereinafter) to drive the assay label over the antibody array (27) and into the waste chamber (30). The fluid plunger (5) in the third chamber (22) is locked at the bottom of its stroke by an internal detent (34). The fluid plunger (5) in the fourth chamber (23) is then actuated at a controlled rate (as described hereinafter) to drive the second wash buffer over the antibody array (27) and into the waste chamber (30). The fluid plunger (5) for the fourth chamber (23) is locked at the bottom of its stroke by an internal detent (34).

The detection instrument (1) is equipped with an electrical power cable and connectivity ports (eg USB ports) to connect to peripherals required for the functionality of the apparatus (eg barcode scanner, printer and local area network). An LED light (660) at the front of the detection instrument (1) displays a colour-based status eg Ready (Green), Busy (Yellow), Test Completed (Blue), Error (Red) or Off (no light). The detection instrument (1) includes optical, proximity or other sensors to confirm the presence of the sample processing device (2). A bar code on the outer surface of the detection instrument (1) is read by a barcode reader located within the detection instrument (1) to confirm expiry date and test type. The detection instrument (1) includes an exterior touch screen (60) which serves as a user interface during set-up and displays instructional prompts, error warnings and test results.

Figure 6B:
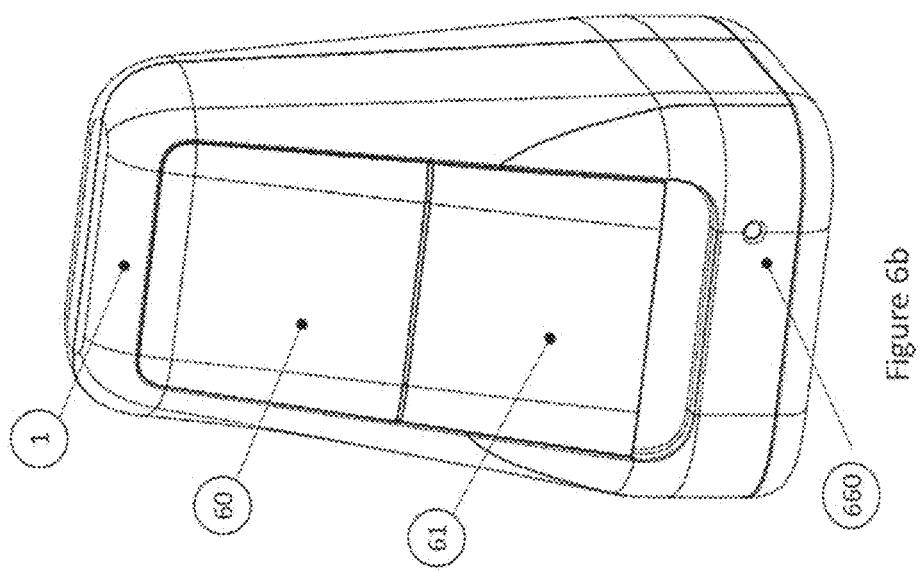
FIGS. 6a and 6b illustrate the embodiment of the biochemical assay apparatus before and after the door of the detection instrument is closed.
Figure 6A:
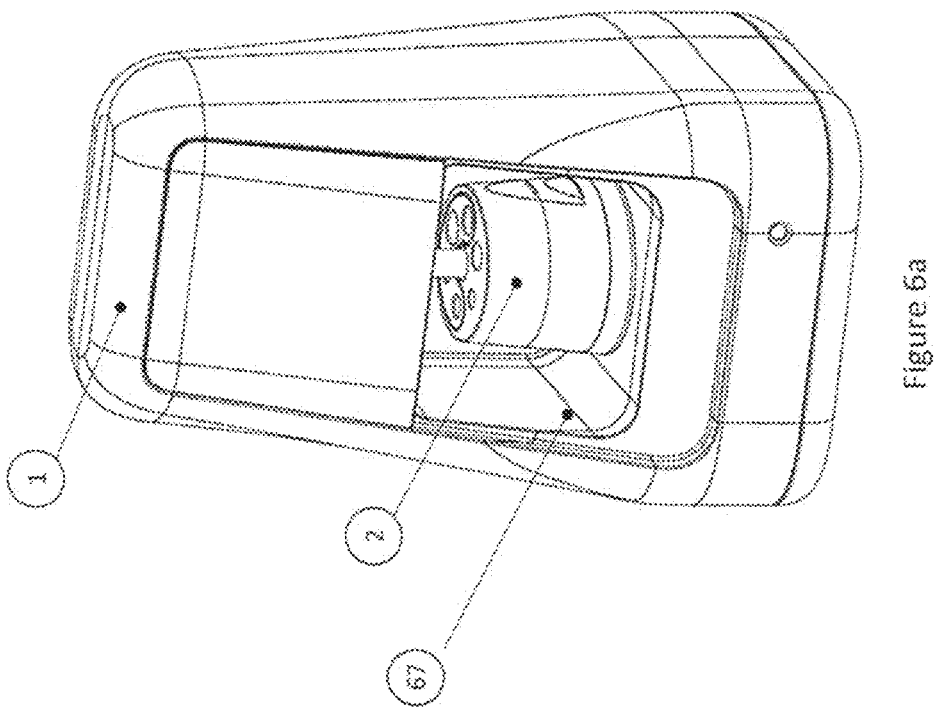

With reference to FIG. 6a, the detection instrument (1) includes an enclosure (67) in which the sample processing device (2) is located with the vessel rack (3) deployed and the vacutainer (12) depressed. A door (61) closes the enclosure (67) during the test (see FIG. 6b) to prevent the user interfering with the sample processing device (2) and to shield the optics from ambient light.

Figure 6C:
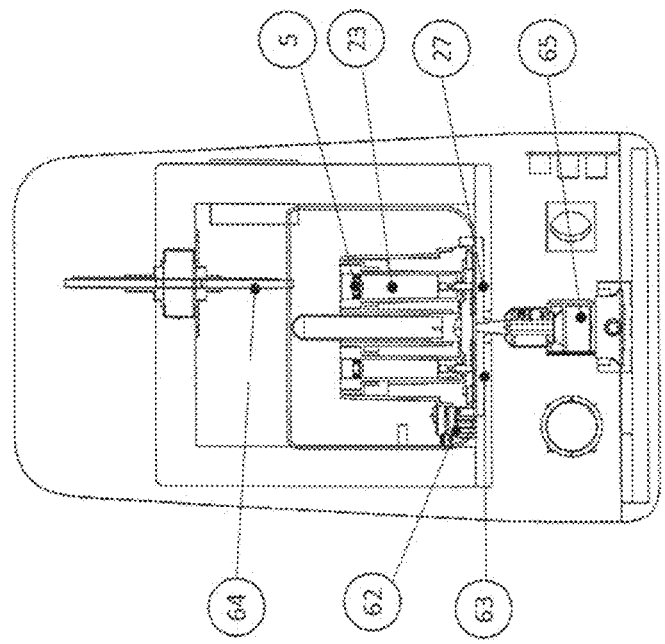
FIGS. 6c and 6d illustrate cross-sectional views of the embodiment of the biochemical assay apparatus.
Figure 6D:
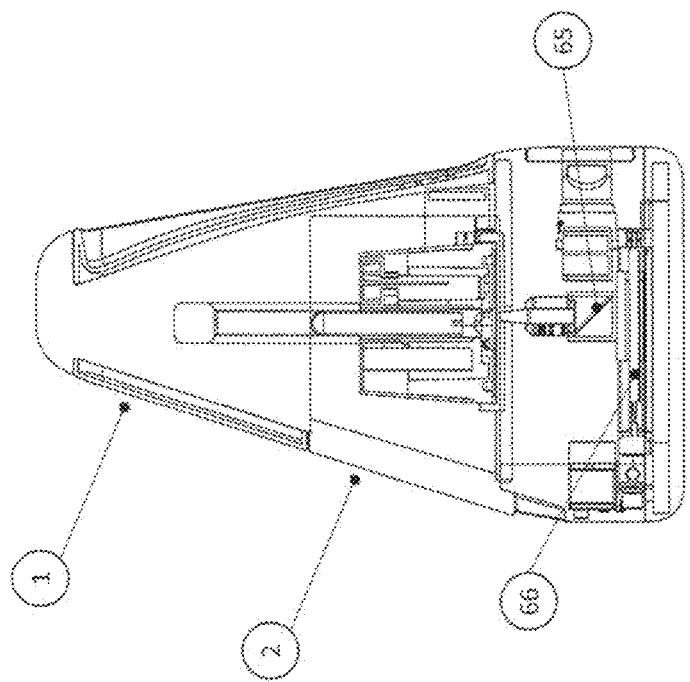

The detection instrument (1) includes a rotary actuator (62) that drives a rotary platform (63) which mechanically interfaces with the sample processing device (2) located in the enclosure (67) (see FIGS. 6c and 6d). The rotary actuator (62) rotates the rotary platform (63) and the sample processing device (2) to predetermined rotary positions that enable the sequential actuation steps described above for the air plunger (18), the valve plunger (52) and each fluid plunger (5). For this purpose, the air chamber (17), valve compartment (24) and the first, second, third and fourth chambers (19, 21, 22 and 23) define a pitch circle with a common diameter so that as the sample processing device (2) rotates, the air plunger (18), the valve plunger (52) and the fluid plunger (5) of each of the first, second, third and fourth chambers (19, 21, 22 and 23) is aligned under a linear actuator (64). The linear actuator (64) and rotary platform (63) include position sensors to enable them to work together to actuate the fluid plungers (5), the air plunger (18) or the valve plunger (52) in each of the predetermined rotary positions.

In the basal part of the detection instrument (1) is located an optical module (65) which is a fluorescent optical system that images the bottom surface of the antibody array (27). Components of the optical module (65) are mounted on a linear stage (66) such that the full area of the antibody array (27) can be imaged when the sample processing device (2) is rotated.

FIGS. 7a-c illustrate alternative embodiments of the sample processing device (2) which differ in height to allow reduced sample volumes without affecting operation. FIG. 7a corresponds to FIG. 3c and uses a vacutainer (12) for testing (for example) 10 ml of whole blood. FIG. 7b illustrates a low volume sample processing device (2a) suitable for testing (for example) 0.5 ml of neonatal blood or 0.1 ml of cerebrospinal fluid. FIG. 7c illustrates a large volume sample processing device (2b) suitable for testing (for example) 10 ml of urine.

FIG. 8 outlines schematically the steps carried out to execute a biochemical assay on a biological fluid sample in the biological assay apparatus of the invention. The fluid reagents and the required volumes are shown in Table 1. The duration of the test is typically in the range of 3 minutes to 6 hours.

TABLE 1

| Fluid reagent | Expected minimum volume | Expected maximum volume |
| --- | --- | --- |
| Dilution buffer | 0.1 ml | 20 ml |
| Wash buffer no. 1 | 0.1 ml | 20 ml |
| Assay Label | 0.1 ml | 20 ml |
| Wash buffer no. 2 | 0.1 ml | 20 ml |
| Biological Fluid Sample | 0.1 ml | 20 ml |

FIG. 9 illustrates in cross-section an alternative embodiment of a biochemical assay apparatus of the invention which is designated generally by reference numeral (90). The biochemical assay apparatus (90) comprises a detection instrument (91) which includes an enclosure in which a sample processing device (99) is located. A door (94) closes the enclosure during the test to prevent the user interfering with the sample processing device (99) and to shield the optics from ambient light. The sample processing device (99) is controlled by the detection instrument (91) through a series of linear actuations to execute a biochemical assay on a biological fluid sample.

The sample processing device (99) of the embodiment illustrated in FIG. 9 is shown in a disassembled state in FIG. 10. The sample processing device (99) is a single-use consumable which contains the fluid reagents (eg functionalised elements, buffers and labels) necessary to execute the biochemical assay on the biological fluid sample. The sample processing device (99) comprises a housing (101) and a vessel carrier (103) vertically restrainable in a rack compartment of the housing (101).

The vessel carrier (103) acts as a box-like collar for four mutually spaced apart substantially cylindrical syringe vessels (104) which together form a vessel rack. Each syringe vessel (104) is mounted in the vessel carrier (103) by adhesive or mechanical connection (eg a threaded, push-fit or snap-fit connection). Each syringe vessel (104) is equipped at its foot end with a syringe end cap (164) and at its head end with a non-return plunger (105). The four syringe vessels (104) define respectively a first chamber for a dilution buffer, a second chamber for a first wash buffer, a third chamber for an assay label and a fourth chamber for a second wash buffer.

The housing (101) is coupled to a manifold (117) through its base (107). The manifold (117) contains a fluid circuit which is able to fluidly couple the first, second, third and fourth chambers to an antibody array (127) (see FIG. 11) mounted sealingly beneath the floor of the manifold (117). The fluid circuit is sealed from the chambers of the syringe vessels (104) until the point of use when it is selectively fluidly connected to each syringe vessel (104). The housing (101) additionally defines an air chamber (221) sealed by an air plunger (222) and a valve compartment for an array valve. The air chamber (221) and valve compartment are accessible respectively through apertures in the lid of the housing (101). The air chamber (221) is mounted on the base (107) by adhesive or laser welding.

An array inlet port (280) in the antibody array (127) is normally isolated from the fluid circuit by the array valve which is located upstream from the array inlet port (280). The antibody array (127) comprises a zig-zag channel (240) which creates a continuous fluid pathway between the array inlet port (280) and an array outlet port (290) from where fluid is discharged into a waste chamber (150) in the peripheral region of the manifold (117). Antibodies are attached to the walls of the channel (240). An array cover (191) is mounted on the base of the antibody array (127).

The detection instrument (91) includes a movable platform (98) which mechanically interfaces with the sample processing device (99) located in the enclosure. The movable platform (98) and the sample processing device (99) are moved to predetermined x-y positions that enable sequential actuation steps for the air plunger (222), a valve plunger (147) and each non-return plunger (105). As the sample processing device (99) moves, the air plunger (222), the valve plunger (147) and the non-return plunger (105) of each of the first, second, third and fourth chambers is aligned under a linear actuator (911) on an actuator frame (910). The linear actuator (911) and movable platform (98) include position sensors to enable them to work together to actuate the non-return plungers (105), the air plunger (222) or the valve plunger (147) in each of the predetermined x-y positions.

At the point-of-use, the vessel rack is depressed to a non-elevated (deployed) position and sequential actuation steps carried out at predetermined x-y positions are similar to those described hereinbefore for the embodiment of FIG. 1. In the non-elevated (deployed) position, the vessel rack is restrained by the housing (101).

A needle (300) pierces the syringe end cap (164) to open a fluid pathway between the syringe vessel (104) and the fluid circuit in the manifold (117). The sample processing device (99) is loaded with a standard vacutainer (212). The vacutainer (212) containing a biological fluid sample is inserted into the sample processing device (99) through a vacutainer port (202). The manifold (117) contains a vacutainer latch (187) which prevents a user from connecting the vacutainer (212) directly to the fluid circuit in the manifold (117) and a pair of needles (167) which punctures the septum of the vacutainer (212). A first of the pair of needles (167) is in fluid communication with the air chamber (221) and a second of the pair of needles (167) is in fluid communication with the first chamber which contains the dilution buffer. When the air plunger (222) is actuated, air from the air chamber (221) is forced into the vacutainer (212) via the second of the pair of needles (167) and flushes the biological fluid sample into the first chamber containing the dilution buffer via the first of the pair of needles (167).

The array valve is opened by actuating the displacement of the valve plunger (147). With the array valve open, the fluid circuit in the manifold (117) is able to couple selectively the chambers to the antibody array (127). Firstly the non-return plunger (105) in the first chamber is actuated at a controlled rate and the diluted sample is evacuated into the fluid circuit. The diluted sample is then delivered via the array valve through the array inlet port (280) into the antibody array (127). Fluid exits the antibody array (127) through an array outlet port (290) and is discharged into the waste chamber (150).

The non-return plunger (105) in the second chamber is then actuated at a controlled rate to drive the first wash buffer over the antibody array (127) and into the waste chamber (150). The non-return plunger (105) in the third chamber is then actuated at a controlled rate to drive the assay label over the antibody array (127) and into the waste chamber (150). The non-return plunger (105) in the fourth chamber is then actuated at a controlled rate to drive the second wash buffer over the antibody array (127) and into the waste chamber (150). A PTFE frit (106) is included in the top of the waste chamber (150) to relieve air pressure.

In the basal part of the detection instrument (91) is located an optical module (97) which is a fluorescent optical system that images the bottom surface of the antibody array (127). The optical module (97) is switched on using an exterior switch (95) and functionality is provided by a printer (93), scanner (92) and screen (999). The detection instrument (91) is further provided with a handle (96) for portability.

The invention claimed is:

1. A biochemical assay apparatus for assaying a biological fluid sample comprising:
    a detection instrument which comprises:
    an enclosure;
    a movable platform in the enclosure selectively movable to a plurality of positions;
    a linear actuator mounted in the enclosure above the movable platform and actuatable along a linear axis;
    a sample processing device mounted or mountable on the movable platform in the enclosure which comprises:
    a manifold;
    a compartmentalised housing mounted on the manifold and capable of receiving the biological fluid sample in an elongate fluid compartment, wherein the compartmentalised housing has a valve compartment, a rack compartment and an elongate air chamber which is sealed by an air plunger;
    a rack of elongate vessels mounted in the rack compartment at an elevated non-deployed position or at a non-elevated deployed position, wherein each elongate vessel defines a fluid chamber which is sealed by a fluid plunger, wherein the rack of elongate vessels is movable from the elevated non-deployed position to the non-elevated deployed position to cause the elongate vessels to fluidly connect to the manifold;
    an antibody array mounted beneath a floor of the manifold such that the manifold is able to fluidly couple each elongate vessel selectively to the antibody array; and an array valve which has a closed position which isolates the elongate vessels from the antibody array and an open position which fluidly connects the elongate vessels to the antibody array via the manifold,
  wherein when the rack of elongate vessels is in the non-elevated deployed position, the movable platform is moved sequentially to selected ones of the plurality of positions,
wherein in an initial position of the plurality of positions, the linear actuator is coaxial with the elongate air chamber whereby on actuation the linear actuator is configured to depress the air plunger in order to cause air from the elongate air chamber to enter the elongate fluid compartment and to flush the biological fluid sample into a first fluid chamber of a first elongate vessel of the rack of elongate vessels containing a first diluent reagent to form a diluted biological fluid sample,
  wherein in a first position of the plurality of positions, the linear actuator is coaxial with the first fluid chamber of the first elongate vessel whereby on actuation the linear actuator depresses the fluid plunger of the first elongate vessel to cause the diluted biological fluid sample to enter the antibody array via the manifold,
  wherein in a second position of the plurality of positions, the linear actuator is coaxial with a second fluid chamber of a second elongate vessel of the rack of elongate vessels whereby on actuation the linear actuator depresses the fluid plunger of a second elongate vessel to cause a wash reagent to enter the antibody array via the manifold and
  wherein in a third position of the plurality of positions, the linear actuator is coaxial with a third fluid chamber of a third elongate vessel of the rack of elongate vessels whereby on actuation the linear actuator depresses the fluid plunger of the third elongate vessel to cause an assay label reagent to enter the antibody array via the manifold.

2. A biochemical assay apparatus as claimed in claim 1 wherein the movable platform is a rotary platform selectively rotational to a plurality of rotary positions.

3. A biochemical assay apparatus as claimed in claim 1 wherein the movable platform is an x-y platform selectively movable to a plurality of x-y positions.

4. A biochemical assay apparatus as claimed in claim 1, wherein in a fourth position of the plurality of positions, the linear actuator is substantially coaxial with a fourth fluid chamber of a fourth elongate vessel of the rack of elongate vessels whereby on actuation the linear actuator depresses the fluid plunger of the fourth elongate vessel to cause an additional wash reagent to enter the antibody array via the manifold.

5. A biochemical assay apparatus as claimed in claim 1, wherein the array valve is an actuatable array valve mounted in the valve compartment.

6. A biochemical assay apparatus as claimed in claim 5 wherein when the rack of elongate vessels is in the non-elevated deployed position, the movable platform is additionally movable to a valve position of the plurality of positions, wherein in the valve position the linear actuator is substantially coaxial with the valve compartment whereby on actuation the linear actuator actuates the actuatable array valve to the open position to fluidly connect the elongate vessels and the antibody array via the manifold.

7. A biochemical assay apparatus as claimed in claim 1, wherein the antibody array is mounted sealingly beneath the floor of the manifold.

8. A biochemical assay apparatus as claimed in claim 1, wherein the antibody array includes one or more channels which create a continuous fluid pathway between an array inlet port and an array outlet port, wherein antibodies are attached to the walls or floor of the channel.

9. A biochemical assay apparatus as claimed in claim 1, wherein prominences are provided on the walls or floor of the channel, wherein the prominences are mutually spaced apart.

10. A biochemical assay apparatus as claimed in claim 8, wherein the fluid pathway is a spiral or zig-zag fluid pathway.

11. A biochemical assay apparatus as claimed in claim 8, wherein the fluid is discharged from the array outlet port into a waste chamber in the manifold.

12. A biochemical assay apparatus as claimed in claim 1, wherein the manifold contains a fluid circuit which is able to fluidly couple each of the elongate vessels to the antibody array.

13. A biochemical assay apparatus as claimed in claim 1, wherein the rack of elongate vessels comprises a plurality of substantially cylindrical vessels mutually spaced apart and connected at their neck portions by a collar.

14. A biochemical assay apparatus as claimed in claim 1, wherein in the elevated non-deployed position, the rack of elongate vessels is seated in the rack compartment and each elongate vessel is aligned with and spaced apart from a spigot or needle projecting upwardly from the floor of the manifold, wherein the rack of elongate vessels is depressed to a non-elevated deployed position such that the foot end of the elongate vessel is penetrated by the spigot or needle.

15. A biochemical assay apparatus as claimed in claim 1, wherein the manifold contains a first and second hollow needle projecting upwardly from its floor.

16. A biochemical assay apparatus as claimed in claim 2 wherein the air chamber, the valve compartment and the first, second, third and fourth chambers define a pitch circle with a substantially common diameter, wherein when the sample processing device is mounted on the rotary platform, the pitch circle is intersected by the linear axis of the linear actuator so that as the sample processing device rotates, the air plunger, the valve plunger and the fluid plunger of each of the first, second, third and fourth chambers is substantially aligned beneath the linear actuator.

17. A biochemical assay apparatus as claimed in claim 3 wherein the air chamber, the valve compartment and the first, second, third and fourth chambers define a rectangular array, wherein when the sample processing device is mounted on the x-y platform, the rectangular array is intersected by the linear axis of the linear actuator so that as the sample processing device moves, the air plunger, the valve plunger and the fluid plunger of each of the first, second, third and fourth chambers is substantially aligned beneath the linear actuator.

18. A biochemical assay apparatus as claimed in claim 1, wherein the antibody array comprises a control zone on to which a probe capture ligand is immobilised and a first major surface on which two or more test zones are defined, wherein a first test zone has immobilised thereon a first pathogen-specific antibody adapted to bind to a first capture target on a first pathogen or marker, wherein a second test zone has immobilised thereon a second pathogen-specific antibody adapted to bind to a second capture target on a second pathogen or marker.

19. A sample processing device as defined in claim 1.

20. A detection instrument as defined in claim 1.

21. An antibody array as defined in claim 1.

* * * * *